United States Patent [19] [11] 4,082,745
Borrevang et al. [45] Apr. 4, 1978

[54] PROCESS FOR THE PREPARATION OF PHOSPHORUS DERIVATIVES OF SECONDARY AMMONIUM SALTS OF PENAM AND CEPHEM COMPOUNDS

[75] Inventors: Poul Borrevang, Rodovre; Erling Guddal, Skovlunde; Henning Borge Petersen, Lyngby; Peter Faarup, Frederiksberg; Jorgen Ilum Nielsen, Farum, all of Denmark

[73] Assignee: Novo Industri A/S, Bagsvaerd, Denmark

[21] Appl. No.: 669,048

[22] Filed: Mar. 22, 1976

[30] Foreign Application Priority Data

Mar. 26, 1975 United Kingdom ............... 12788/75
Jun. 24, 1975 United Kingdom ............... 26826/75

[51] Int. Cl.² .................. C07D 499/14; C07D 501/04
[52] U.S. Cl. ..................................... 260/239.1; 544/17
[58] Field of Search ......................... 260/243 C, 239.1

[56] References Cited

U.S. PATENT DOCUMENTS

| 3,926,954 | 12/1973 | Kiesewetter et al. | 260/243 C |
| 3,932,391 | 1/1976 | Alburn et al. | 260/243 C |
| 3,953,436 | 4/1976 | Spry | 260/243 C |
| 3,962,215 | 6/1976 | Sellstedt | 260/243 C |
| 3,994,883 | 11/1976 | Borrevang et al. | 260/243 C |
| 3,994,911 | 11/1976 | Sellstedt | 260/243 C |

Primary Examiner—Donald G. Daus
Assistant Examiner—David E. Wheeler
Attorney, Agent, or Firm—Fidelman, Wolffe & Waldron

[57] ABSTRACT

An improvement in the conversion of penam and cephem compounds to secondary ammonium salts of phosphite amides thereof by reacting as follows:

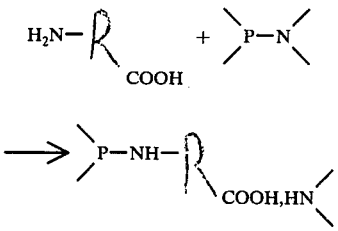

wherein —R, is the non-reacting balance of the penam or cephem compound and

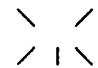

are non-reacting substituents.

Catalytic amounts of H—N< or the hydrogenhalide thereof may be present in the reaction medium.

6 Claims, No Drawings

PROCESS FOR THE PREPARATION OF PHOSPHORUS DERIVATIVES OF SECONDARY AMMONIUM SALTS OF PENAM AND CEPHEM COMPOUNDS

This invention relates to the conversion of penam and cephem compounds characterized by presence of an $NH_2$ group and a COOH group thereon into a secondary ammonium salt of a phosphite amide of the penam or cephem compound.

Overall this conversion is shown to be a useful approach for transferring readily available penam and cephem compounds, into more desired compounds.

The conversion may be illustrated by simplified formulae, as follows:

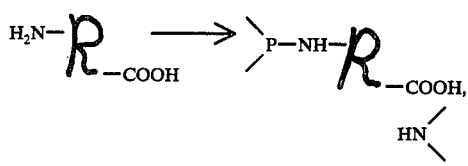

wherein R corresponds to the non-reacting balance of the penam and cephem compounds; and

are employed to indicate non-reacting substituents

The present invention involves carrying out the conversion by reacting with a phosphite amide, as follows:

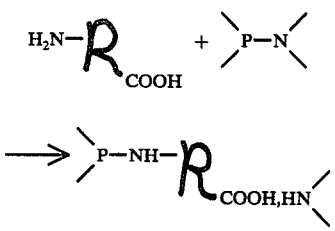

As can be seen from the formula sequence the phosphite group reacts with the $H_2N-$ of the penam or cephem compound and the amino group from the phosphite amide reacts with the $-COOH$ group of the penam or cephem compound to form the secondary ammonium salt.

This invention contemplates also an addition of silyl halide, either as one of the initial reactants or as a subsequent reaction reactant. In either event the silyl ester of the phosphite penam or cephem is formed

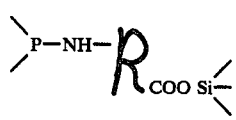

where, the

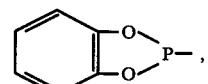

is employed to indicate non-reacting substituents.

The invention will now be described in more detail and with reference to penam and cephem compounds of particular interest. More specifically, this invention relates to a novel process for the preparation of secondary ammonium salts of phosphite amides of penam and cephem compounds having the general formula:

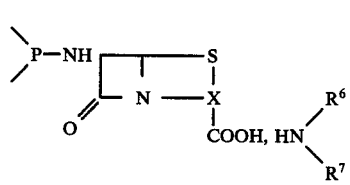

in which $>P-$ is selected from the group consisting of:

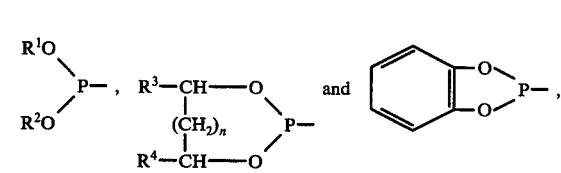

in which
$R^1$ and $R^2$ are different or identical alkyl groups containing 1-5 carbon atoms,
$R^3$ and $R^4$ are different or identical, each representing a hydrogen atom or a methyl group,
$n$ is 0 or 1,
X is selected from the group consisting of

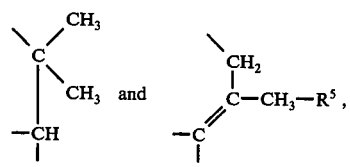

in which $R^5$ represents a hydrogen atom or an acetoxy group,
and
$R^6$ and $R^7$ which may be different or identical, are selected from the group consisting of alkyl containing 1-5 carbon atoms and cycloalkyl containing 5-6 ring carbon atoms, or $R^6$ and $R^7$ form together with the nitrogen atom of the secondary amino group a 5-7 membered heterocyclic ring, optionally containing an additional hetero atom, by reacting a compound having the general formula:

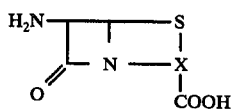

wherein X has the meaning defined above, with a phosphite amide of the general formula:

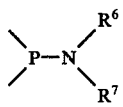

wherein > P—, $R^6$ and $R^7$ have the meanings defined above, in an inert solvent,
and optionally converting the carboxylic ammonium salts thus obtained into the corresponding silyl esters.

A number of phosphite amides of the above general formula (I) are disclosed in our pending U.S. patent application, Ser. No. 427,363 now U.S. Pat. No. 3,994,883. These phosphite amides have proved to be valuable intermediates for the preparation of synthetic derivatives of the penicillin and cephalosporin group of antibiotics. We have found these intermediates to be particularly valuable for the acylation of 7-amino-$\Delta^3$-cephem esters with acyl halides. These esters are very easily isomerized to the corresponding $\Delta^2$- derivatives under the influence of bases as shown in J. Chem. Soc. (C) (1966) 1142 and J.A.C.S. 91 (1969) 1401. As disclosed in the above identified patent application we are able to acylate under neutral conditions and thus to avoid this undesirable isomerization. The only process disclosed so far for the preparation of compounds of the general formula (I) is the process disclosed in the above identified patent application. According to said process, the secondary ammonium salt of the amino-penam or -cephem carboxylic acid is reacted with a halogenophosphite in the presence of one additional equivalent of the secondary amine

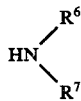

which serves the purpose of neutralizing the hydrogen halide generated during the condensation. This process may be exemplified by the following Scheme 1 which illustrates the preparation of a phosphite amide derived from the diethylammonium salt of 6-APA:

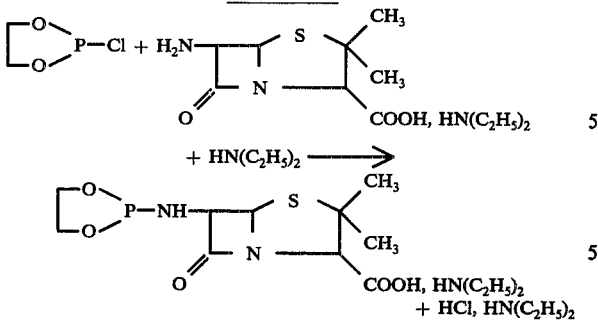

The process described above suffers from some disadvantages, particularly when performed on an industrial scale. Thus, it has been found necessary to purify the halogenophosphite meticulously in order to minimize the formation of by-products during the subsequent steps of the reaction in order to facilitate the work-up and recovery of the final product. The purification of the halogenophosphite — particularly when the aim is to eliminate degradation products — may require fractional distillation. However, due to corrosive properties and pungent odour of the halogenophosphites, the distillation and handling in general of the halogenophosphites is inconvenient to such an extent that their replacement by other and less hazardous chemicals is desirable.

Furthermore, to suppress undesirable side reactions, such as attack by excess of the secondary amine on the β-lactam ring, the condensation with halogenophosphite according to Scheme 1 must necessarily be performed at low temperature, e.g. $-20°$ C, thus adding the cost of cooling the reaction mixture to the other disadvantages mentioned above.

These shortcomings of the prior art process are eliminated by the novel process of the present invention.

Without imposing any restrictions on the general scope of the present invention, the following Scheme 2 illustrates the novel process, providing the phosphite amide derivative of 6-APA identical to that of Scheme 1 above:

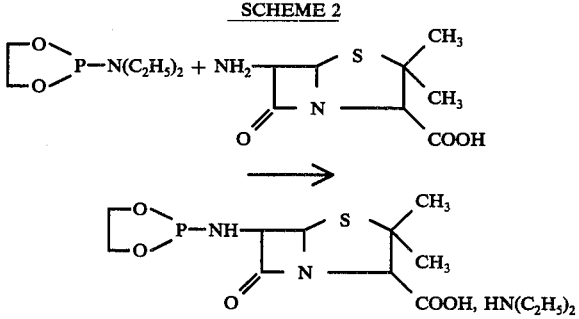

The reactants for the process of the invention are preferably used in equimolar amounts. The reaction can be performed within the temperature range of 0° C–100° C. A wide range of commonly used solvents are applicable, e.g. acetonitrile, methylene chloride, chloroform and benzene.

Since the amino-penam and-cephem carboxylic acids are slightly soluble in these solvents the reaction rate may be increased by addition of a catalytic amount of an amine, preferably about 5 mole percent of the amine

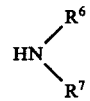

from which the phosphite amide used in the reaction is derived.

Alternatively, the reaction of Scheme 2 may be catalyzed by addition of an ammonium salt, preferably a hydrogen halide of the amine

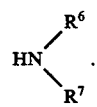

The phosphite amides of the general formula III may be prepared according to the method of H. J. Lucas et al. (J.A.C.S. 72 (1950) p. 5495) by reacting the corresponding halogenophosphite with two equivalents of the secondary amine

These phosphite amides are less corrosive, less prone to hydrolysis and have a higher storage stability than the corresponding halogenophosphites. These properties are particularly advantageous in connection with their use in an industrial process.

The utilization of intermediates of the general formula (I) in the preparation of penicillin and cephalosporin derivatives is disclosed in the above identified pending U.S. patent application. The following schemes illustrate the synthesis of ampicillin:

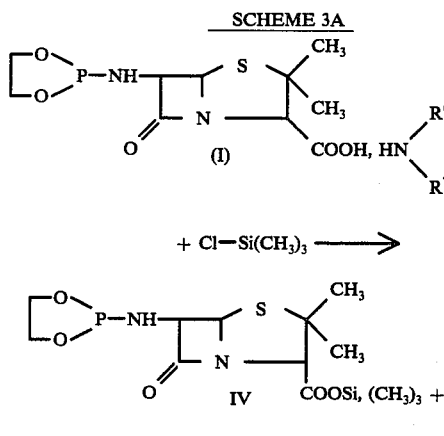

The intermediate (I) is first reacted with trimethylchlorosilane, thus affording an almost quantitative yield of the silyl ester IV. Without isolation, the silyl ester may be reacted with an activated acid derivative e.g. D(—)-α-phenylglycyl chloride hydrochloride, followed by hydrolysis, to form ampicillin in a yield of about 90%.

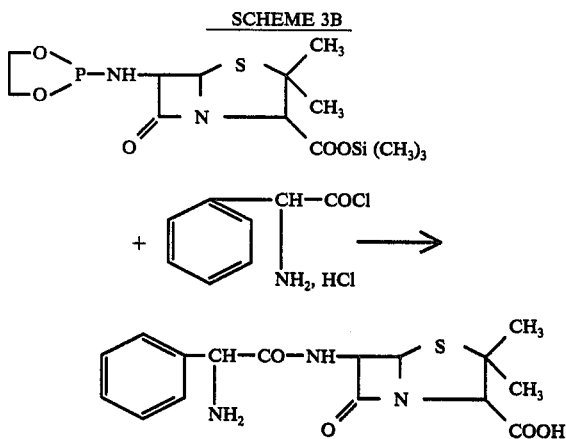

Alternatively, the silyl ester IV may be prepared in high yield in the absence of a catalyst by adding trimethylchlorosilane simultaneously or immediately following the addition of the phosphite amide to 6-APA, according to the following scheme:

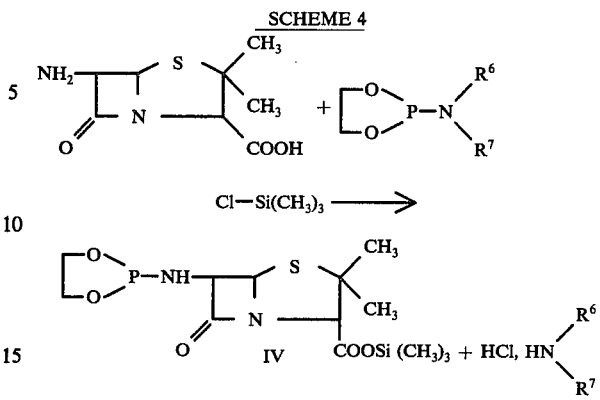

This modification of the reaction conditions presents considerable technical advantages. Thus, a several fold increase of the over-all reaction rate is observed, and, at the same time, an extremely pure form of the intermediate IV is obtained, thus resulting in an increased yield after the subsequent acylation step.

The preparation of ampicillin outlined above merely serves as an illustration of the utilization of the intermediates of the general formula (I) prepared by the process of the present invention. In principle the syntheses of other penam and cephem antibiotics proceed in analogous manner. The invention will now be described in further detail with reference to the following examples. The halogenophosphite method for the preparation of the diethylammonium salts of 6-ethylenephosphiteamidopenicillanic acid (Example 1) and 7-ethylenephosphiteamido-3-methylceph-3-em-4-carboxylic acid (Example 5) is disclosed in Examples 5 and 6, respectively, of the above identified, pending U.S. patent application Ser. No. 427,363.

EXAMPLE 1

Diethylammonium salt of 6-ethylenephosphiteamido-penicillanic acid.

2.16 g (10 millimoles) of 6-aminopenicillanic acid are suspended in 25 ml dry acetonitrile. 1.63 g (10 millimoles) of 2-diethylamino-1,3,2-dioxaphospholane and 0.05 ml (0.5 millimole) diethylamine are added.

After 17 hours of stirring under nitrogen, a solution of the diethylammonium salt of 6-ethylenephosphiteamido-penicillanic acid is obtained.

NMR (CH$_3$CN) shows the following characteristic signals relative to TMS:

| δ ppm | | |
|---|---|---|
| 1,20 (t) | $J \simeq 7,5$ Hz | N(CH$_2$CH$_3$)$_2$ |
| 1.51 (s) | | (2) C(CH$_3$)(CH$_3$) |
| 1.58 (s) | | |
| 2,87 (q) | $J \simeq 7,5$ Hz | N(CH$_2$CH$_3$)$_2$ |
| 3,98 (s) | | (3) C—H |
| 3.6–4,4 (m) | | H$_2$C—O, H$_2$C—O, P— |
| 4,88 (multiplet consisting of 8 peaks) | $J_{HCCH} \simeq 4,3$ Hz, $J_{HCNP} \simeq 11,8$ Hz | $J_{HCNH} \simeq 6,4$ Hz (6) C—H |
| 5,36 (d) | $J_{HCCH} \simeq 4,3$ Hz | (5) C—H |

The solution contains the product in an amount corresponding to 95 – 100% of the theoretical amount, and can be used directly without purification in the synthesis of penicillins.

EXAMPLE 2

Diisopropylammonium salt of 6-ethylenephosphiteamido-penicillanic acid.

2.16 g (10 millimoles) of 6-aminopenicillanic acid are suspended in 25 ml dry methylene chloride. 1.8 ml (10 millimoles) of 2-diisopropylamino-1,3,2-dioxaphospholane and 0.07 ml (0.5 millimole) of diisopropylamine are added. After 20 hours of stirring under nitrogen, a solution of the diisopropylammonium salt of 6-ethylenephosphiteamidopenicillanic acid is obtained. The solution can be used directly without purification in the synthesis of penicillins.

In order to analyse the product obtained, the solution is concentrated in vacuum and dissolved in deuterochloroform.

The IR spectrum of the solution shows characteristic bands at 1770 cm$^{-1}$ (—CO—, β-lactam), 1630 cm$^{-1}$ (COO$^-$) and 1020 cm$^{-1}$ (POC).

NMR of the solution shows the following characteristic signals relative to TMS:

| δ ppm | | |
|---|---|---|
| 1,32 (d) | J ≃ 6.5 Hz | (CH(CH$_3$)$_2$)$_2$ |
| 1,65 (2 × s) | | (2) C$\diagup^{CH_3}_{\diagdown CH_3}$ |
| 3,2 (h) | J ≃ 6.5 Hz | (CH(CH$_3$)$_2$)$_2$ |
| 4,2 (s) | | (3) C—H |
| 3,7–4,3 (m) | | H$_2$C—O$\diagdown$ <br> \| $\quad\quad$ P <br> H$_2$C—O$\diagup$ |
| 4,85 (multiplet consisting of 8 peaks) | | |
| | J$_{HCCH}$≃ 4,5 Hz, | (6) C—H |
| | J$_{HCNP}$≃ 12,0 Hz | |
| 5,53 (d) | J ≃ 4,5 Hz | (5) C—H |

EXAMPLE 3

Diethylammonium salt of 6-(4-methyl-1,3,2-dioxaphospholan-2-yl-amino) penicillanic acid.

1.08 g (5 mmol) of 6-aminopenicillanic acid are suspended in 10 ml of dry deuterochloroform. 0.886 g (5 mmol) of 2-diethylamino-4-methyl-1,3,2-dioxaphospholane and one drop of diethylamine are added.

After 1½ hours of stirring at 30° C followed by an additional 1 hour at 50° C, a solution of the diethylammonium salt of 6-(4-methyl-1,3,2-dioxaphospholan-2-yl-amino) penicillanic acid is obtained in nearly quantitative yield.

NMR (CDCl$_3$) shows the following characteristic signals relative to TMS:

| δ ppm | |
|---|---|
| 1,1–1,53 (t and d) | N(CH$_2$CH$_3$)$_2$ <br> CH$_3$ <br> $\diagdown$CH — O$\diagdown$ <br> \| $\quad\quad$ P <br> CH$_2$—O$\diagup$ |
| 1,57 (s) | (2) C$\diagup^{CH_3}_{\diagdown CH_3}$ |
| 1,62 (s) | |
| 2,9 (q) | J≃7 Hz $\quad$ N(CH$_2$CH$_3$)$_2$ |
| 4,12 (s) | (3) C—H |
| 3,2–4,55 (m) | CH$_3$ <br> $\diagdown$CH — O$\diagdown$ <br> \| $\quad\quad$ P <br> CH$_2$—O$\diagup$ |
| 4,75 (multiplet consisting of 8 peaks) | (6) C—H |
| 5,38 (d) | J$_{HCCH}$≃ 4,4 Hz $\quad$ (5) C—H |

EXAMPLE 4

Diethylammonium salt of 6-(1,3,2-dioxaphosphorinan-2-yl-amino) penicillanic acid.

1.08 g (5 mmol) of 6-aminopenicillanic acid are suspended in 10 ml dry deuterochloroform. 0.886 g (5 mmol) of 2-diethylamino-1,3,2-dioxaphosphorinane and one drop of diethylamine are added.

After 1½ hours of stirring at 30° C followed by an additional 1 hour at 50° C, a solution of the diethylammonium salt of 6-(1,3,2-dioxaphosphorinan-2-yl-amino) penicillanic acid is obtained in nearly quantitative yield.

NMR (CDCl$_3$) shows the following characteristic signals relative to TMS:

| δ ppm | | |
|---|---|---|
| 1,3 (t) | J ≃ 7,6 Hz | N(CH$_2$CH$_3$)$_2$ |
| 1,60 (s) }<br>1,67 (s) } | | (2) C$\diagup^{CH_3}_{\diagdown CH_3}$ |
| 2,9 (q) | J ≃ 7,5 Hz | N(CH$_2$CH$_3$)$_2$ |
| 4,18 (s) | | (3) C—H |
| 3,5–4,6 (m) | | H$_2$C—O$\diagdown$ <br> \| $\quad\quad$ P— <br> H$_2$C$\diagdown$ $\diagup$O <br> $\quad$C <br> $\quad$H$_2$ |
| 4,9 (multiplet consisting of 8 peaks) | | |
| | J$_{HCCH}$≃ 4,4 Hz | |
| | J$_{HCNH}$≃7,5 Hz | (6) C—H |
| | J$_{HCNP}$≃ 12,0 Hz | |
| 5,42 (d) | J$_{HCCH}$≃ 4,4 Hz | (5) C—H |

EXAMPLE 5

Diethylammonium salt of 7-ethylenephosphiteamido-3-methyl-ceph-3-em-4-carboxylic acid.

2.14 g (10 millimoles) of 7-aminodesacetoxycephalosporanic acid are suspended in 25 ml dry acetonitrile.

1.63 g (10 millimoles) of 2-diethylamino-1,3,2-dioxaphospholane and 0.10 ml (1 millimole) of diethylamine are added. After 4 hours refluxing, a solution of the diethylammonium salt of 7-ethylenephosphiteamido-3-methyl-ceph-3-em-4-carboxylic acid is obtained. It contains an amount corresponding to 75 – 90% of the theoretical amount.

NMR (CH$_3$CN) shows the following characteristic signals relative to TMS:

| δ ppm | | |
|---|---|---|
| 1,20 (t) | J ≃ 7,5 Hz | N(CH₂CH₃)₂ |
| 3—CH₃ is hidden under CH₃CN | | |
| 2,85 (q) | J ≃ 7,5 Hz | N(CH₂CH₃)₂ |
| 3,2 (AB system) | | (2) CH₂ |
| 3,5–4,5 (m) | | H₂C—O<br>  \<br>   P<br>  /<br>H₂C—O |
| 4,6–5,2 (m) | | (6) CH |
| | | (7) CH |

The solution can be used directly in the synthesis of cephalosporins.

EXAMPLE 6

Diethylammonium salt of 7ethylenephosphiteamido-cephalosporanic acid 1.36 g (5 millimoles) of 7-aminocephalosporanic acid are suspended in 25 ml dry chloroform. 0.82 g (5 millimoles) of 2-diethylamino-1,3,2-dioxaphospholane and 0.05 ml (0.5 millimole) of diethylamine are added.

After 17 hours of stirring under nitrogen at room temperature, a solution of the diethylammonium salt of 7-ethylenephosphiteamido-cephalosporanic acid is obtained.

NMR (CHCl₃) shows the following characteristic signals relative to TMS:

| δ ppm | | |
|---|---|---|
| 1,3 (t) | J ≃ 6,5 Hz | N(CH₂CH₃)₂ |
| 2,05 (s) | | O—CO—CH₃ |
| 2,93 (q) | J ≃ 6,5 Hz | N(CH₂CH₃)₂ |
| 3,2 (d) | J ≃ 18 Hz | (2) —CH₂— |
| 3,5 (d) | J ≃ 18 Hz | |
| 3,5–4,2 (m) | | H₂C—O<br>  \<br>   P—<br>  /<br>H₂C—O |
| 4,82 (d) | J ≃ 13 Hz | (3) C—CH₂—O |
| 5,14 (d) | J ≃ 13 Hz | |
| 4,9 (d) | J ≃ 4,5 Hz | (6) C—H |
| 4,8 (multiplet partially hidden by the above-mentioned signals) | | (7) C—H |

According to the NMR spectrum there is no detectable amount of the Δ²-isomer.

The solution can be used without purification in the synthesis of cephalosporins.

EXAMPLE 7

Trimethylsilyl 6-ethylenephosphiteamido-penicillanate.

2.16 g (10 millimoles) of 6-aminopenicillanic acid are suspended in 25 ml dry acetonitrile. 1.63 g (10 millimoles) of 2-diethylamino-1,3,2-dioxaphospholane and 1.09 g (10 millimoles) of trimethylchlorosilane are added under stirring at room temperature. After 30 minutes of stirring under nitrogen, a solution of trimethylsilyl 6-ethylenephosphiteamido-penicillanate is obtained.

The IR spectrum (CH₃CN) shows characteristic bands at 1780 cm⁻¹ (—CO—, β-lactam), 1720 cm⁻¹ (—CO—, ester), and 1015 cm⁻¹ (POC). NMR of the solution shows the following characteristic signals relative to TMS.

| δ ppm | | |
|---|---|---|
| 0,28 (s) | | Si(CH₃)₃ |
| 1,51 (s) | } | (2) C<br>  / \<br>CH₃ CH₃ |
| 1,60 (s) | } | |
| 4,31 (s) | | (3) C—H |
| 3,7–4,5 (m) | | H₂C—O<br>  \<br>   P<br>  /<br>H₂C—O |
| 5,00 (multiplet consisting of 8 peaks) | J_{HCCH}≃ 4,5 Hz,<br>J_{PNCH}≃ 12,0 Hz | J_{HCNH}≃ 6,8 Hz,<br>(6) C—H |
| 5,48 (d) | J_{HCCH}≃ 4,5 Hz | (5) C—H |

The solution contains the product in an amount corresponding to 95 – 100% of the theoretical amount and can be used directly without purification in the synthesis of penicillins.

EXAMPLE 8

Trimethylsilyl 7-ethylenephosphiteamido-cephalosporanate 1.36 g (5 millimoles) of 7-aminocephalosporanic acid are suspended in 15 ml dry acetonitrile. 0.82 g (5 millimoles) of 2-diethylamino-1,3,2-dioxaphospholane and 0.55 g (5 millimoles) of trimethylchlorosilane are added under stirring at room temperature.

After 6 hours of stirring under nitrogen a filtered sample of the solution shows the following characteristic signals relative to TMS:

| δ ppm | | |
|---|---|---|
| 0,4 (s) | | Si (CH₃)₃ |
| (3) —O—CO—CH₃ is hidden under the signal from CH₃CN | | |
| 3,30 (d) | J ≃ 18 Hz | (2) —CH₂— |
| 3,65 (d) | J ≃ 18 Hz | |
| 3,7–4,3 (m) | | H₂C—O<br>  \<br>   P—<br>  /<br>H₂C—O |
| 4,63 (d) | J ≃ 13 Hz | (3) —CH₂—O— |
| 4,95 (d) | J ≃ 13 Hz | |
| 4,87 (d) | J ≃ 4,5 Hz | (6) —C—H |
| 5,10 (multiplet consisting of 8 peaks) | J_{HCCH}≃ 4,5 Hz,<br>J_{PNCH}≃ 11,6 Hz | J_{HNCH}≃ 6,9 Hz<br>(7) C—H |

There is no detectable amount of Δ² -isomer in the NMR spectrum.

The IR spectrum of the same solution shows characteristic bands at 1780 cm⁻¹ (—CO—, β-lactam), 1745 cm⁻¹ (—CO—, acetylester), 1710 cm⁻¹ (—CO—, silylester), 1640 cm⁻¹ (Δ-3-double bond) and 1020 cm⁻¹ (POC).

The solution contains trimethylsilyl 7-ethylenephosphiteamido-cephalosporanate in an amount corresponding to 95–100% of the theoretical amount.

The precipitated diethylammoniumchloride can be removed by filtration or the suspension can be used without purification in the synthesis of cephalosporins.

EXAMPLE 9

Ampicillin trihydrate.

A mixture of 2.16 g (10 millimoles) of 6-APA, 1.49 ml (1.63 ml ∼ 10 millimoles) of 2-diethylamino-1,3,2-dioxaphospholane, and 1.27 ml (10.1 millimoles) of chlortrimethylsilane is stirred at room temperature for 1 hour. At the end of this period, 6-APA has been totally dissolved. After cooling to 0° C, 2.16 g (10.5 millimoles) of phenylglycylchloride, hydrochloride, are added under continued stirring. Th stirring is continued at 0° C for further 40 minutes. An analysis of the reaction product shows that an acylating yield of about 90% of the theoretical amount has been obtained. After removal of precipitated diethylamine, hydrochloride by filtration, the reaction mixture is added slowly and while stirring to 50 ml of ice water, the pH value of the mixture being maintained at 4.9 by addition of 6 N NaOH. A precipitation of needle-shaped crystals of ampicillin trihydrate is initiated after a few minutes. After filtration, washing of remanence on the filter with ice water and drying. 2.46 g of pure crystalline ampicillin trihydrate corresponding to 61% of the theoretical yield are obtained.

0.56 g of crystalline ampicillin trihydrate is subsequently recovered from the filtrate in a manner which is well known per se. The total yield obtained during the synthesis was 75 % of the theoretical yield.

EXAMPLE 10 p-Hydroxyampicillin 3.42 g of finely powdered 6-aminopenicillanic acid are dispersed in 25 ml of dry methylene chloride, and 1.9 ml of trimethylchlorosilane (15 millimoles) and 2.68 ml (15 millimoles) of 2-diisopropylamino-1,3,2-dioxaphospholane are added. An exothermic reaction starts, whereby the temperature rises to about 30° C. The reaction mixture is stirred at room temperature for three hours, then cooled to 0° C. 2.9 g (25 millimoles) of pyridine hydrochloride, 2.66 g (10 millimoles) of D-(-)-p-trimethylsilyloxyphenylglycine-N-carboxyanhydride, and 1.15 g (10 millimoles) of N-hydroxysuccinimide are added, and the mixture stirred overnight at 0° C. A solution of 6.7 g of sodium dioctyl-sulfosuccinate in 50 ml of ethyl acetate are added, and the precipitated salts are removed by filtration. The methylene chloride is evaporated in vacuo, and the solution poured into 25 ml of ice water containing 0.75 ml of 85% phosphoric acid. The phases are separated, and the aqueous phase extracted twice with 10 ml of ethyl acetate containing 1.67 g of sodium dioctylsulfosuccinate. The combined organic extracts are added to 10 ml of water, and the pH is adjusted to 5.2 by addition of dicoco-monomethylamine, and the mixture is stirred for one hour at 0° C to complete the precipitation of the product. 3.13 g (75%) of p-hydroxyampicillin trihydrate are isolated by filtration. One reprecipitation from water at isoelectric pH produces the pure compound, showing IR and NMR spectra identical with those of authentic material.

EXAMPLE 11

7β-D(÷)α-phenylglycylamido)-3-methyl-ceph-3em-4-carboxylic acid (Cephalexin)

8.56 g (40 millimoles) of 7-aminodesacetoxycephalosporanic acid are suspended in 200 ml of dry methylene chloride. 6.0 ml (50 millimoles) of dimethyldichlorosilane are then added, and subsequently, 6.52 g (40 millimoles) of 2-diethylamino-1,3,2-dioxaphospholane are added. The mixture is stirred at room temperature for 1 hour, and is then refluxed for 3 hours. Finally, the mixture is stirred at room temperature for 20 hours. The reaction mixture is cooled to −10° C, and 10.7 g (52 millimoles) of D-(÷)α-phenylglycylchloride, hydrochloride, are added. The mixture is stirred at −10° C for 3 hours, and subsequently, at room temperature for 1 hour. The mixture is poured into 300 ml water containing ice, and is stirred for 30 minutes. Subsequently, the pH value is adjusted at 7.0 with 30% sodium hydroxide solution, and the organic phase is separated. The aqueous phase is evaporated in vacuum to 200 ml, the pH value adjusted to 5.7 with 6 N hydrochloric acid, and during a period of 2 hours, a solution of 11.5 g (80 millimoles) of β-naphthol in 20 ml acetone is added dropwise. The precipitate formed is removed by filtration and washed with water and n-butylacetate. 16.0 g of a cephalexin -β-naphthol complex are formed. The cephalexin is liberated by dissolving the complex in 50 ml water and 50 ml n-butylacetate by means of 6 N sulfuric acid (pH 1.5).

The aqueous phase is removed and is shaken twice with 50 ml n-butylacetate, and evaporated in vacuum to 35 ml. 35 ml isopropanol are added, and the pH value is adjusted at 4.7 with triethylamine while seeding the mixture with cephalexin monohydrate. The precipitate formed is removed by filtration, washed with isopropanol/water (1:1) and dried. 9.2 g of crystalline cephalexin monohydrate are obtained.

EXAMPLE 12

Cephalothin 2.3 g (8.5 millimoles) of 7-aminocephalosporanic acid are suspended in 25 ml dry acetonitrile. 1.28 ml (8.5 millimoles) of 2-diethylamino-1,3,2-dioxaphospholane and 1.13 ml (8.9 millimoles) of trimethylchlorosilane are added under stirring at room temperature.

After 20 hours the precipitated diethylammonium chloride is removed by filtration under nitrogen.

1.36 g (8.5 millimoles) of 2-thienylacetylchloride are added at 0° C under stirring.

After 1.5 hours, 15 ml of ethylacetate and 10 ml ice are added and the mixture is stirred for 20 minutes. The phases are separated. The water phase is extracted with 10 ml of ethylacetate. The combined organic phases are washed with 10 ml of water. The organic phase is added to 15 ml of water and pH adjusted to 6.1 with 8.3 ml of 1N sodium hydroxide solution. The phases are separated and the water phase is concentrated in vacuum and the product is crystallized with acetone. 2.35 g (66%) of cephalothin are obtained. m.p.: 209° – 210° C (dec).

The IR spectrum (KBr) shows characteristic bands at 3280 cm$^{-1}$ (—NH—), 1750 cm$^{-1}$ (—CO—, β-lactam), 1730 cm$^{-1}$ (—CO—, acetylester), 1655 cm$^{-1}$ (—CO—, amid I), 1620 cm$^{-1}$ (—COO$^-$) and 1530 cm$^{-1}$ (amid II) which are identical with those of authentic material.

NMR (DMSO-d$_6$-D$_2$O) shows signals identical with those of authentic material relative to TMS:

| δ ppm | | |
|---|---|---|
| 2,02 (s) | | (3) —O—CO—CH$_3$ |
| 3,20 (d) | J ≃ 18 Hz | |
| 3,58 (d) | J ≃ 18 Hz | (2) —CH$_2$— |
| 3,80 (s) | | (7) —CO—CH$_2$— |
| 4,8 (d) | J ≃ 13 Hz | |
| 5,0 (d) | J ≃ 13 Hz | (3)—C—CH$_2$—O— |
| 4,95 (d) | J ≃ 4,5 Hz | (6) C—H |
| 5,56 (d) | J ≃ 4,5 Hz | (7) C—H |
| 7,0 (m) | | =HC—CH= |
| 7,4 (m) | | —S—CH= |

There is no detectable amount of the Δ²-isomer in the NMR spectrum.

EXAMPLE 13

Cephalothin.

2.72 g (10 mmol) of 7-aminocephalosporanic acid are suspended in 25 ml of dry methylene chloride. 1,5 ml (10 mmol) of 2-diethylamino-1,3,2-dioxaphospholane are added. 1.33ml (10,5 mmol) of trimethychlorosilane are added at room temperature. The reaction mixture is stirred at this temperature overnight under nitrogen. The mixture is cooled to 0° C and 1.45ml (10 mmol) of 2-thienylacetylchloride are added over a period of 10 minutes under stirring. After stirring for 1.5 hours at 0° C, 30 ml of ethyl acetate and 15 ml of ice-water are added and the mixture is stirred for 20 minutes. The phases are separated. The aqueous phase is extracted with 10 ml of ethyl acetate. The combined organic phases are washed with 10 ml of water. 30 ml of ice-water are added to the organic phase and pH is adjusted to 6,0 with about 5 ml of 2 N sodium hydroxide solution. The phases are separated. The organic phase is extracted with 10 ml of water. The combined aqueous phases are extracted with 15 ml of ethyl acetate and concentrated in vacuum. The sodium salt of cephalothin crystallizes with about one mole of water.

3.85 g (88%) of the crude product are obtained. Melting point: 207°–209° C (dec).

Microbiological assay: 894 μg/mg.

NMR and IR spectra show the same characteristic signals as set forth in example 12.

EXAMPLE 14

Cephacetril.

2.72 g (10 mmol) of 7-aminocephalosporanic acid are suspended in 50 ml of dry methylene chloride. 1.5 ml (10 mmol) of 2-diethylamino-1,3,2-dioxaphospholane and 1.33 ml (10.5 mmol) of trimethylchlorosilane are added under nitrogen at room temperature. The reaction mixture is stirred for 16 hours at room temperature. After cooling to 0° C, a solution of 10 mmol of cyanoacetyl chloride in 6 ml of methylene chloride is added over 5 minutes.

After stirring at room temperature for 2 hours the reaction mixture is concentrated in vacuum. The residue is dissolved in a mixture of 75 ml of ethyl acetate and 100 ml of a 10% solution of $K_2HPO_4$. After stirring for 20 minutes the phases are separated. The aqueous phase is further extracted with 25 ml of ethyl acetate. The combined organic phases are extracted with 25 ml of a 10% solution of $K_2HPO_4$. The aqueous phases are combined and 100 ml of ethyl acetate are added. The pH is adjusted to 2,2 with 2 N hydrochloric acid, and the phases are separated. The aqueous phase is extracted twice with 50 ml of ethyl acetate. The combined organic phases are dried over magnesium sulphate. After evaporation of the solvent in vacuum, 2.9 g of cephacetril are obtained.

The IR spectrum shows the following characteristic bands:

2260 cm⁻¹ (C ≡ N), 1770 cm⁻¹ (—CO—, β-lactam), 1730 cm⁻¹ (—CO—, acetylester), 1670 cm⁻¹ (—CO—, amid I) and 1545 cm⁻¹ (amid II) The NMR spectrum (DMSO-d₆) shows the following signals:

δ ppm

| | | |
|---|---|---|
| 2,05 (s) | | (3) —O—CO—CH₃ |
| 3,41 (d) | J ≃ 18 Hz | (2) —CH₂— |
| 3,74 (d) | J ≃ 18 Hz | |
| 3,77 (s) | | (7) —CO—CH₂ |
| 4,67 (d) | J ≃ 13 Hz | (3) —C—CH₂—O |
| 5,05 (d) | J ≃ 13 Hz | |
| 5,11 (d) | J ≃ 4,5 Hz | (6) —C—H |
| 5,71 (dd) | J ≃ 4,5 Hz | (7) —C—H |
| | J ≃ 8 Hz | |
| 9,25 (d) | J ≃ 8 Hz | (7) —N—H |

EXAMPLE 15

Cephacetril.

5.44 g (20 mmol) 7-aminocephalosporanic acid are suspended in 100 ml of dry methylene chloride. 3.82 g (20 mmol) of 2-diisopropylamino-1,3,2-dioxaphospholane are added under stirring. 2.67 ml (21 mmol) of trimethylchlorosilane are added under stirring at room temperature. The mixture is stirred overnight under nitrogen.

After cooling to 0° C a solution of 20 mmol of cyanoacetyl chloride in 10 ml dry methylene chloride is added over 5 minutes. After 2 hours stirring at room temperature T.L.C. shows only one spot corresponding to cephacetril and no spot for the starting material.

The product is worked up as set forth in example 14. 5.85 g of cephacetril are obtained.

Analysis calculated for $C_{13}H_{13}N_3O_6S$: C: 46.02, H: 3.86, N: 12.38, S: 9.45%; Found: C: 45.56, H: 3.89, N: 12.04, S: 9.38%

The IR and NMR spectra show the same characteristic signals as set forth in example 14.

EXAMPLE 16

Phtalidyl 6-[D(—)α-aminophenylacetamido] penicillanate, hydrochloride.

A mixture of 13.45 ml (75 mmol) of 2-diisopropylamino-1,3,2-dioxaphospholane and 16.20 g (75 mmol) of 6-aminopenicillanic acid in 150 ml dry acetonitrile was stirred for 18 hours at room temperature. The clear solution of 6-ethylenephosphiteamidopenicillanic acid diisopropylammonium salt thus obtained was cooled to 10° C and 15.98 g (75 mmol) of 3-bromophthalide were added portion-wise over 10 minutes. Stirring was continued for 2½ hours at room temperature, at which time esterification was shown by high voltage electrophoresis to be complete.

The temperature was adjusted to 0° C, 15.45 g (75 mmol) of D-(—)α-phenyl glycylchloride, hydrochloride was added in portions over 15 minutes and stirring was continued at 0° C. After 2 hours, 375 ml of a cold saturated aqueous solution of NaCl and 185 ml of ethyl acetate were added and the mixture was stirred for 15 minutes at 0° C. The phases were separated, the organic layer was extracted 3 times with a cold saturated aqueous solution of NaCl, dried and concentrated to dryness in vacuum.

After thorough treatment with 500 ml of ether, the sticky residue was transformed into a white amorphous powder of crystalline appearance which was filtered off, washed with ether and dried for 4 hours in vacuum at 40° C to give 29 g (75%) of phathalidyl 6-[D(—)α-aminophenylacetamido]penicillanate, hydrochloride.

The IR spectrum (KBr disk) shows characteristic absorptions at 1783, 1687, 1498, 1285, 1151, 1051, 980, 896, 755 and 699 cm$^{-1}$.

The NMR spectrum (DMSO-d$_6$) shows signals at:

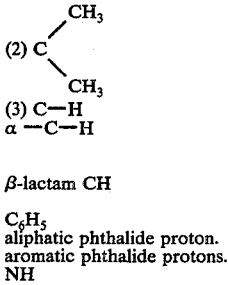

| δ ppm | | |
|---|---|---|
| 1.45 (d) | | (2) C(CH$_3$)(CH$_3$) |
| 4.50 (s) | | (3) C—H |
| 5.11 (s) | | α —C—H |
| 5.48 (m) | | |
| 6 peaks | J$_{HNCH}$ ≃ 6.3 Hz<br>J$_{HCCH}$ ≃ 4.3 Hz | β-lactam CH |
| 7.43 (m) | | C$_6$H$_5$ |
| 7.57 (s) | | aliphatic phthalide proton. |
| 7.81 (m) | | aromatic phthalide protons. |
| 9.4 (d) | J ≃ 6.3 Hz | NH |

In DMSO-d$_6$/D$_2$O the δ 9,4 signal disappears and the δ 5.48 multiplet becomes δ 5.46 (2H, q, J = 4.3 Hz).

What is claimed:

1. In the conversion of 6-amino-penicillanic acid to secondary ammonium salt phosphite amides thereof, the improvement which comprises the steps of reacting 6-aminopenicillanic acid with a member selected from the group consisting of:
   2-diethylamino-1,3,2-dioxaphospholane
   2-diisopropylamino-1,3,2-dioxaphospholane
   2-diethylamino-4-methyl-1,3,2-dioxaphospholane
   2-diethylamino-1,3,2-dioxaphosphorinane,
   the phosphite group reacting with the 6-amino group and the dialkyl amino group reacting with acid group to form the desired secondary ammonium salt.

2. In the conversion of a member selected from the group consisting of 7-aminodesacetoxycephalosporanic acid and 7-aminocephalosporanic acid into the secondary ammonium salt of the 7-ethylenephosphite amide thereof the improvement which comprises the steps of reacting the cephalosporanic acid with a member selected from the group consisting of:
   2-diethylamino-1,3,2-dioxapholane and
   2-diisopropylamino-1,3,2-dioxaphospholane,
   the phosphite group reacting with the 7-amino group and the dialkylamino group reacting with the acid group to form the secondary ammonium salt.

3. The process of claim 2 in which the secondary ammonium salt of the phosphite amide is thereafter reacted with tri-methyl or di-methyl silyl halide without intermediate separation to form the corresponding silyl ester.

4. The process of claim 2 in which the reaction is carried out in the added presence of tri-methyl or di-methyl silyl halide to form the corresponding silyl ester.

5. The process of claim 1 in which the secondary ammonium salt of the phosphite amide is thereafter reacted with tri-methyl or di-methyl silyl halide without intermediate separation to form the corresponding silyl ester.

6. The process of claim 1 in which the reaction is carried out in the added presence of tri-methyl or di-methyl silyl halide to form the corresponding silyl ester.

* * * * *